US010338015B2

(12) United States Patent
Augustine et al.

(10) Patent No.: US 10,338,015 B2
(45) Date of Patent: Jul. 2, 2019

(54) METHODS AND APPARATUS FOR ANALYSIS OF SEALED CONTAINERS

(71) Applicants: The Regents of the University of California, Oakland, CA (US); Madison Avenue Management Co., Inc., Hamburg, NJ (US)

(72) Inventors: Matthew P. Augustine, Davis, CA (US); Victor Lim, Walnut Creek, CA (US); Joseph S. Broz, Alexandria, VA (US)

(73) Assignees: THE REGENTS OF THE UNIVERSITY OF CALIFORNIA, Oakland, CA (US); MADISON AVENUE MANAGEMENT CO., INC., Hamburg, NJ (US)

( * ) Notice: Subject to any disclaimer, the term of this patent is extended or adjusted under 35 U.S.C. 154(b) by 542 days.

(21) Appl. No.: 14/772,068

(22) PCT Filed: Mar. 4, 2014

(86) PCT No.: PCT/US2014/020439
§ 371 (c)(1),
(2) Date: Nov. 30, 2015

(87) PCT Pub. No.: WO2014/138136
PCT Pub. Date: Sep. 12, 2014

(65) Prior Publication Data
US 2016/0003753 A1 Jan. 7, 2016

Related U.S. Application Data

(60) Provisional application No. 61/772,532, filed on Mar. 4, 2013, provisional application No. 61/852,391, filed on Mar. 15, 2013.

(51) Int. Cl.
*G01N 24/08* (2006.01)
*G01R 33/30* (2006.01)
*G01R 33/46* (2006.01)

(52) U.S. Cl.
CPC .......... *G01N 24/084* (2013.01); *G01R 33/30* (2013.01); *G01R 33/4625* (2013.01)

(58) Field of Classification Search
CPC .... A61B 5/055; G01N 24/084; G01N 24/082; G01N 24/085; G01N 24/087;
(Continued)

(56) References Cited

U.S. PATENT DOCUMENTS 6,456,072 B1 * 9/2002 Webb ................... G01R 33/30
324/307
7,355,402 B1 4/2008 Taicher et al.
(Continued)

OTHER PUBLICATIONS

International Search Report corresponding to PCT/US2014/020439 dated Jun. 23, 2014 (3 pages).

*Primary Examiner* — Huy Q Phan
*Assistant Examiner* — Dustin R Dickinson
(74) *Attorney, Agent, or Firm* — Kilpatrick Townsend & Stockton LLP

(57) ABSTRACT

This invention relates to methods and devices for NMR spectroscopy analyzing sealed containers e.g., food and beverage containers and other containers, and particularly according to specific embodiments sealed containers made of a conducting but generally nonferromagnetic metal or other conducting material. As discussed in above referenced applications, many current strategies for contaminant detection require a container to be violated, a process that can destroy the container or product and is impractical in large scale applications. The present invention overcomes these and other problems by providing methods and devices for
(Continued)

the detection of contaminants and/or contraband in metal or conducting containers by NMR spectroscopy.

17 Claims, 10 Drawing Sheets

(58) Field of Classification Search
CPC .. G01R 33/30; G01R 33/307; G01R 33/4608; G01R 33/4625; G01R 33/4616
See application file for complete search history.

(56) References Cited

U.S. PATENT DOCUMENTS

| | | | |
|---|---|---|---|
| 2004/0251904 A1* | 12/2004 | Corver | G01N 24/08 324/321 |
| 2005/0024052 A1 | 2/2005 | Bendall et al. | |
| 2006/0091883 A1* | 5/2006 | Mikhaltsevitch | G01R 33/441 324/318 |
| 2006/0192557 A1* | 8/2006 | Kloza | G01N 24/08 324/318 |
| 2007/0001673 A1 | 1/2007 | Augustine et al. | |
| 2008/0292554 A1 | 11/2008 | Ahrens | |
| 2011/0050223 A1* | 3/2011 | Balcom | G01R 33/305 324/307 |
| 2012/0119738 A1 | 5/2012 | Hiller et al. | |
| 2012/0133358 A1 | 5/2012 | Broz | |
| 2012/0206141 A1* | 8/2012 | Apostolos | G01N 24/084 324/309 |
| 2012/0223706 A1 | 9/2012 | Hetherington et al. | |

\* cited by examiner

METHODS AND APPARATUS FOR ANALYSIS OF SEALED CONTAINERS

STATEMENT AS TO RIGHTS TO INVENTIONS MADE UNDER FEDERALLY SPONSORED RESEARCH AND DEVELOPMENT

This invention was made with government support under HSHQDC-11-C-00006 awarded by Department of Homeland Security. The government has certain rights in the invention.

CROSS-REFERENCE TO RELATED APPLICATIONS

This application is a continuation of International Patent Application No. PCT/US2014/020439, filed Mar. 4, 2014, which claims priority to U.S. Provisional Pat. Appl. No. 61/772,532, filed on Mar. 4, 2013, and U.S. Provisional Pat. Appl. No. 61/852,391, filed on Mar. 15, 2013, the disclosures of which are herein incorporated by reference in their entirety for all purposes. This application incorporates by reference the following U.S. patents for all purposes: U.S. Pat. Nos. 7,339,377, 6,911,822, 7,012,427, and incorporates by reference all documents referenced therein for background and all other purposes.

FIELD OF THE INVENTION

This invention relates to methods and devices for NMR spectroscopy analyzing sealed containers e.g., food and beverage containers and other containers, and particularly according to specific embodiments sealed containers made of a conducting but generally non-ferromagnetic metal or other conducting material.

BACKGROUND OF THE INVENTION

As discussed in above referenced applications, many current strategies for contaminant detection require a container to be violated, a process that can destroy the container or product and is impractical in large scale applications. The present invention overcomes these and other problems by providing methods and devices for the detection of contaminants and/or contraband in metal or conducting containers by NMR spectroscopy. These methods are equally applicable to other sealed metal containers for which contamination, degradation, or other changes in product flavor or quality is a concern.

SUMMARY OF THE INVENTION

Conventional high resolution nuclear magnetic resonance (NMR) spectroscopy and magnetic resonance imaging (MRI) can be used to study samples in non-metal, diamagnetic, non-conducting containers and to provide a chemical characterization or identification of at least some components of those samples. In the case of NMR spectroscopy, sample containers constructed from glass, quartz, sapphire, and plastic are commercially available.

High resolution NMR has not, however, been effectively applied to metal containers. This is largely due to shielding of the radio frequency (RF) signal in broadcast and received directions caused by metal containers. This shielding (or attenuation) is sometimes expressed as the RF penetration depth (or skin depth) d. Skin depth d generally indicates how far radio waves penetrate into metal (throughout this discussion, metal shall be understood to indicate an example of a conducting non-ferromagnetic material unless the context requires otherwise) under various power/frequency conditions. As is well understood in the art, at higher RF frequencies the skin depth is smaller, thus reducing the amount of RF energy that can be transmitted through the metal.

High resolution NMR has generally be thought to require very high static magnetic field strengths (e.g. about 1.8-25 T or higher) in order for an applied RF signal to generate enough of a precession signal, with sufficient separation, to detect substances of interest. However, as is known in the art, high static magnetic field strengths require high frequency RF signals to provide NMR resonance. These high frequency RF signals (e.g., 300-500 MHz) are however heavily shielded (or attenuated) by conducting containers, making it difficult or impossible to use NMR to examine the contents of such containers. The present invention provides methods and apparatus for the analysis of sealed conducting containers by NMR spectroscopy by using static magnetic field strengths commonly thought too low for high resolution NMR. The invention accomplishes this according to specific embodiments by using shaped RF pulses with frequencies low enough to effectively pass through the conducting container but, in part due to their shape, with sufficient signal in the container to cause precession under the selected static magnetic field. The static magnetic fields and radiofrequency (RF) used in the NMR according to specific embodiments in no way affect the contents of the containers examined via the methods provided herein.

In some embodiments, the present invention provides non-invasive, non-destructive analytical methods for determining various parameters or characteristics of material in sealed containers, e.g., the level of wine acetification in sealed wine containers, the level of a containment or compound or substance indicating spoilage in sealed beverage containers sealed large quantity milk or fruit or vegetable juice containers, sealed meat or cheese or other foodstuffs, other containers, etc., as well as the presence of explosives or contraband materials hidden in such containers. As such, the methods and devices of the present invention can be routinely used in the evaluation of foodstuffs and other materials and in the forensic examination of materials in containers for dangerous or contraband substances. These methods of intact container analysis are not limited to any one detection, but can be extended to the study and/or detection of components and/or contaminants and/or contraband in other types of sealed containers. Any substance or mixture having components that generate an NMR signal that can provide information of interest can be assessed using the methods and devices of the present invention. Thus, a variety of metallic or non-metallic conducting containers purportedly having, for example, nonalcoholic beverages, alcoholic beverages, beer, vinegar olive oil, cheese, meat, vegetable juices or pastes, fruit juices or pulp, or any other substance of foodstuff that can generate a characteristic NMR signal stored therein, can be analyzed using the methods of the present invention.

According to specific embodiments, methods or systems described herein include elements configured to make chemically resolved $^1$H NMR spectroscopy possible in metal non-ferrous cans and to take advantage of one or more of the following: (1) RF metal penetration increases at lower frequencies; (2) the determination by the inventors that RF attenuation by a metal shield is less effective in the near versus far field and thus RF frequencies and therefore static magnetic field strengths previously believed unworkable for metal containers can be used; (3) low power broadband adiabatic or similar pulses created from metal shielded high power RF pulses can be used to efficiently induce free precession signals inside of metal containers; and (4) a frequency and field external reference standard (e.g., a $^{19}$F heteronuclear, $^{23}$Na, $^{2}$H or any material, that provides a good NMR reference signal etc.) can be used rather than an internal or other standard. It has been determined by the inventors that in specific embodiments, it is desirable to have a reference substance with a Lamor frequency far enough away from the Lamor frequency of the detection substance, but close enough to use effectively the same tank circuit and other systems for providing the excitation pulse. Other embodiments, using two coils for example, may use different reference frequencies or use a validated container or substance as a reference frequency.

In specific example embodiments, spectral referencing of the $^{1}$H NMR signal is accomplished using an external frequency reference that is generally placed within the NMR probe. In specific example implementations, an $^{19}$F NMR response from pure perfluorocyclohexane held in a separate small glass (or other appropriate material for NMR samples) container mounted inside of the RF coil immediately below the metal beverage container is used to provide an external frequency reference. According to specific embodiments, an approximately 350 kHz difference in Larmor frequency between $^{1}$H and $^{19}$F nuclei at an example applied 980 G (Gauss) static magnetic field allows for external spectral referencing with just one transmitter and one RF tank circuit. In specific embodiments, the reference RF pulse is a more standard square wave as the container for the reference signal is non-conducting. When using a validated sample as a reference, however, a similar or identical Adiabatic or similar pulse is used.

It will be understood from the teachings provided herein that various RF frequencies and power, and various static magnetic field strengths, can be used in systems and methods of the invention when selected according to the teachings provided herein. In specific example embodiments, however, a frequency and amplitude modulated RF pulse centered around 2 MHz to 5 MHz and broadcast into the container at about 0.5 to 10 kilowatts is used. Lower frequencies can be used so long as the provide enough of an NMR signal to make the chemical resolutions or distinctions desired. Powers as high as practical or achievable for a particular system can also be used, and at higher power in some instances, higher RF frequencies can be used. Generally, the frequency selected, the detection substance, and the static magnetic field strength must be related as indicated by the Lamar equation as will be understood in the art.

The methods of the present invention can be used in a qualitative or quantitative manner, e.g., either the presence of a selected component or the concentration of the selected component is determined. For example, in the analysis of wines or other fermented or similar products, exemplary selected components include, but are not limited to, acetic acid, aldehydes, flavenoids, and amino acids. In the analysis of other foodstuffs, such as milk, juice, cheese, meat, fruit and/or nut and/or vegetable products, etc., various substances indicating spoilage or adulteration can be detected. The methods of the present invention can further also be used for detection of contraband substances, such as explosives, in various containers, quickly and without penetrating or damaging the containers.

The methods of the present invention include the step of positioning a portion of a container or all of a container within a data collection region of the NMR probe. For example, either the neck or top of the container or a portion of the body of the container can be placed within the data collection region of the NMR probe. For flexible bag containers, such as flexible laminated milk or juice or vegetable product containers, a portion of the bag may be situated in the probe. The homogeneous static magnetic field is then established across the data collection region by, for example, adjusting the one or more shim coils in the probe as known in the art or any other technique for NMR static field maintenance or adjustment. Preferably, establishing the homogeneous field allows for resolution of chemical shift difference between selected NMR spectra peaks a minimum distance apart, however, according to specific embodiments, lower than standard magnetic fields are used to allow lower frequency RF signals that more effectively penetrate the conducting material of the container. Methods described herein also involve applying shaped RF pulses selected to penetrate a metallic container and cause a sufficient nuclear precession signal that can be detected by the RF coils outside of the container.

The present invention also provides NMR probes configured to position a portion of a sealed container within an NMR spectrometer. The NMR probes used in the present invention can be configured to primarily detect any of a number of NMR detection nuclei, including, but not limited to, $^{1}$H, $^{2}$H, $^{13}$C, $^{17}$O, or a combination thereof or a reference probe such as $^{19}$F. The NMR probe components include a body structure having a cavity adapted for receiving a portion of the sealed container (e.g., a neck or top of a metallic bottle or can, or a body of a metallic container). The cavity is typically disposed in the body structure (either at a first end, or in a middle portion), such that a first RF coil attached to the body structure is positioned proximal to the cavity and the portion of the sealed container. In one specific embodiment of the probes of the present invention, the first RF coil comprises a single solenoid coil or tubular coil, as illustrated in FIG. 1, In other specific embodiments of the probes of the present invention, the first RF coil comprises a split solenoid coil, in which the coil portions are positioned to either side of the data collection region of the probe. In an alternate embodiment, the first RF coil is a birdcage-style coil surrounding the data collection region of the probe.

Optionally, the NMR probe of the system is a single resonance probe selected to detect one or more substances from the group consisting of $^{1}$H, $^{2}$H, $^{13}$C, $^{17}$O, $^{19}$F, $^{23}$Na, $^{27}$Al, $^{199}$Hg, and $^{207}$Pb.

In some embodiments of the present invention, the first RF coil is used for both transmitting and receiving RF pulses. Optionally, the probe includes a second RF coil positioned distal to the first RF coil. The second RF coils can be, for example, configured for measurement of one or more signals from a calibration sample, for example a sample of an unadulterated or unspoiled substance. Optionally, the second coil can be used to collect an NMR response from a reference sample as described herein. Alternatively, the second RF coil is configured for selective excitation of a second substance or a heteronucleus, such as $^{13}$C, $^{17}$O, $^{19}$F, $^{2}$H, $^{23}$Na, $^{27}$Al, $^{199}$Hg, or $^{207}$Pb.

The probes of the present invention further include a tuning capacitor as will be understood in the art coupled at a first position to the RF coil, and coupled at a second position to a length of coaxial cable configured for connection to the NMR spectrometer. The tuning capacitor can include, but is not limited to, one or more non-magnetic zero-to-ten (0-10) picofarad high power RF capacitors.

Optionally, the probe also includes additional components useful for NMR analyses, such as electronic components for generating magnetic field gradients, a calibration fluid sample tube; and a fluid jacket for modulating the probe temperature, to name a few.

Systems for analyzing contents of a sealed container are also provided by the present invention. The system components include, but are not limited to, the NMR probe configured to position a portion or all of a sealed container within an NMR spectrometer; an NMR spectrometer having a bore proximal to a magnet and configured to receive the NMR probe, an amplifier coupled to the NMR probe via co-axial cable; and a receiver system having a preamplifier and a detector. Optionally, the system further includes a pulse programmer and/or controller and/or control console able to produce an amplitude and frequency modified RF pulse as described herein.

The NMR probe is configured to accept the sealed container and position a portion or all of the container within the magnetic field of the spectrometer. Typically, the spectrometer comprises a wide bore magnet; in some embodiments, the magnetic field is generated by a room temperature or superconducting magnet.

While various magnetic field strengths can be used in the system of the present invention, generally lower than typical NMR field strengths are selected according to specific embodiments to allow for RF resonance frequencies in a lower frequency range able to penetrate metal containers. This is in contrast to previous high resolution NMR, where higher magnetic field strengths were generally preferred to lower field strengths, using the teachings herein effective chemical NMR can be performed using lower magnetic field strengths. These issued are addressed according to specific embodiments as discussed below.

Thus, a magnetic field strengths of around 4.7 T might be selected for chemical NMR, such field strengths require relative high frequency RF signals, such as 400 MHz. According to specific embodiments, lower field strengths, such as 930 G (or 0.0930 T) are used, allowing for RF signals of about 4 MHz.

While the specific embodiments were developed and tested using metallic conducting containers, the methods and systems as taught herein have applications to a variety of NMR systems, including systems used to examine non-conducting containers. Thus, the methods described herein may be used in any situation where it is desired to use lower static magnetic field strengths and lower RF and/or any NMR situation where it is desired to use an external frequency reference.

BRIEF DESCRIPTION OF THE DRAWINGS

FIG. 15 panels A, B and C provide exemplary RF pulse sequences that may be used for conducting NMR analyzes according to specific embodiments.

DETAILED DESCRIPTION

Definitions

Figure 1:
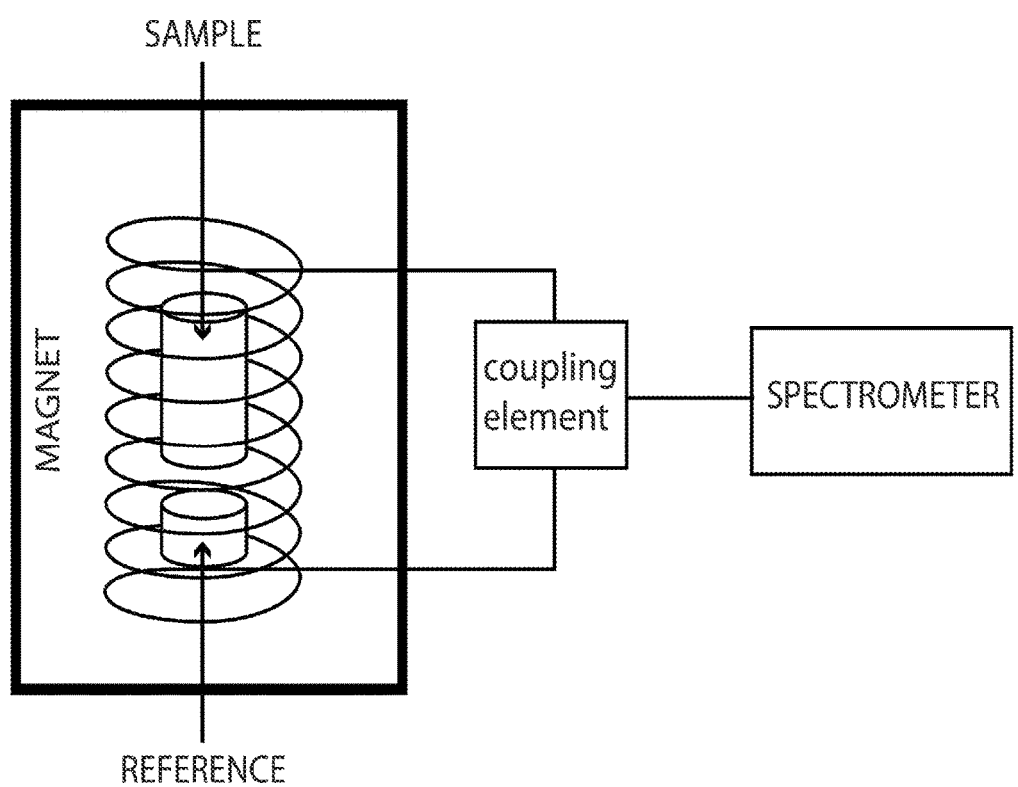
FIG. 1 is a schematic drawing of an exemplary probe of the present invention showing a metallic container and a reference sample in a single coil NMR probe according to specific embodiments.

Before describing the present invention in detail, it is to be understood that this invention is not limited to particular devices or container systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a capacitor" includes a combination of two or more capacitors; reference to a "coil" includes mixtures or series of coils, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "contained materials" as used herein refers to a food, beverage, alternate energy source (e.g., bacterial media) intended for consumption by an organism (e.g., a human, an animal, a cell culture, and the like), or any other item or material that might be sealed in any container or vessel as described herein. Thus, the term "sealed container" refers to a packaged or unopened vessel or receptacle containing the food or beverage or other "contained materials." Sealed NMR tubes prepared with samples of food or beverage products are not considered sealed containers with respect to the present invention.

The terms "NMR probe" and "probe head" are used interchangeably herein to refer to the component of an NMR spectrometer system which transmits pulses to the sample and receives the NMR signals generated.

The term "data collection region" refers to the portion of the NMR probe in which the NMR signal is generated; typically, the homogeneity of the magnetic field of the spectrometer is optimized in this region.

The term "RF coil" refers to a set of filamentary wire sections arranged in a helical geometry and designed for transmitting and/or receiving radiofrequency signals.

The term "tuning capacitor" as used herein refers to one or more capacitor components of the NMR probe which are typically used to match and tune the probe to the correct Larmor frequency and impedance match the RF circuit to, for example, 50Ω.

The term "Larmor frequency" refers to the angular frequency with which an angular momentum vector $\vec{J}$ precesses about an external field axis. Generally, each nuclear isotope has a unique Larmor frequency at a particular static magnetic field strength that can be used for detection using NMR spectroscopy.

The term "split solenoid coil" (or "split pair solenoid") refers to a solenoid having multiple coils of wire (usually in cylindrical form) that generates a magnetic field when carrying a current.

Methods

The present invention provides methods of analyzing one or more contents of a sealed container. The sealed container can be any of a number of food or beverage or other consumer or retail or wholesale containers having contents of interest, including, but not limited to, alcoholic or non-alcoholic beverages, oils, milk, cheese, fruit and other consumables, industrial or household plastics or cleaners or other substances. In a preferred embodiment, the container is a metal container, such as an aluminum can, box, bottle or bag, or a laminated container including conductive materials in the packaging.

The methods of analyzing one or more contents of the sealed container employ an NMR spectrometer and an NMR probe configured to accept a portion (e.g., a portion, a neck, or all) of the sealed container. In the methods of the present invention, the selected portion of the sealed container is positioned within the data collection region of the NMR probe. This can be achieved by placing the container within the probe, and then inserting the probe into the spectrometer, such that the selected portion of the container is positioned within the magnetic field of the spectrometer. Alternatively, the probe can be installed into the spectrometer prior to insertion of the container. In either case, the container is positioned such that a portion of the contents is positioned within the magnetic field of the spectrometer, and proximal to the RF coil of the NMR probe.

A homogeneous static magnetic field is established across the data collection region of the NMR probe by standard NMR mechanisms, e.g., by adjustment of cryogenic and/or room temperature (RT) magnetic field shims. The NMR spectrum is then collected by monitoring the response of the sample to an RF electromagnetic field pulse generated by the RF coil. For shielding containers, especially, the RF pulse is shaped as described herein to overcome attenuation of the RF signal by the container material. According to specific embodiments, the static magnetic field strength and RF pulse frequency(ies) are selected to allow detection in conducting containers or in other situations where a lower magnetic field strength is desired. Preferably, the magnetic field established is homogeneous enough to allow for resolution of chemical shift differences between selected NMR spectra peaks set a minimum distance apart. The degree of homogeneity necessary will depend on a number of factors, including nuclei selection, magnetic field strength, and chemical structure.

In some methods as described herein, the homogeneous static magnetic field is established such that one or more peaks of interest from the contaminant are resolved from additional NMR spectral peaks or using an external reference. For example, for $^1H$ NMR spectra collected on the contents of sealed wine bottles, the minimum desired resolution is approximately 1 ppm, the distance between the methyl resonance and the methylene resonance of the acetic acid contaminant. Exemplary NMR spectra of a number of compounds can be found, for example, in the *Aldrich Library of $^1H$ and $^{13}C$ FT NMR Spectra*, Edition I (1993, volumes 1-3, eds. Pouchert and Behnke, Aldrich Chemical Company).

After an NMR spectrum is collected, the spectrum is examined. Typically, the analysis involves either examination of previously-identified peaks in a select region of the spectrum or analysis of the signal as a whole and may also involve examination of a signal from an external frequency reference. The peaks or overall signal shape can represent any of a number of components found in the sealed container. For example, wine components such as aldehydes or flavenoids can be examined. Foodstuffs or beverages in metal cans can be examined for various containments or spoilage. Sealed containers can also be examined for contraband such as explosives or drugs.

Where the magnetic field is not stabilized with a flux-locked loop, and a $^2H$ lock (as typically employed with small volume NMR samples "spiked" with a deuterated standard such as TMS) is not possible for sealed containers, data collection is typically performed via block averaging (e.g., n data sets of free induction decay each derived from m scans). In a preferred embodiment, the data are collected as block averages of n=10 groups of 100 scans. The n=10 free induction signals are Fourier transformed, overlapped by shifting the frequency, and added offline using software such as Matlab (Mathworks Inc, Natick Mass.) or any similarly capable system. This procedure eliminates the effect of the long time drift in the static magnetic field on the collected data, thereby producing highly resolved $^1$H NMR spectra.

Figure 6:
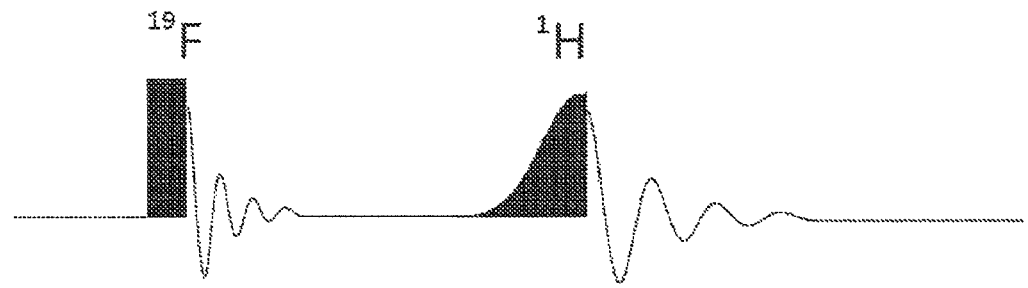
FIG. 6 illustrates two RF pulses and two received precession signals as an example of one system according to specific embodiments.
Figure 7A:
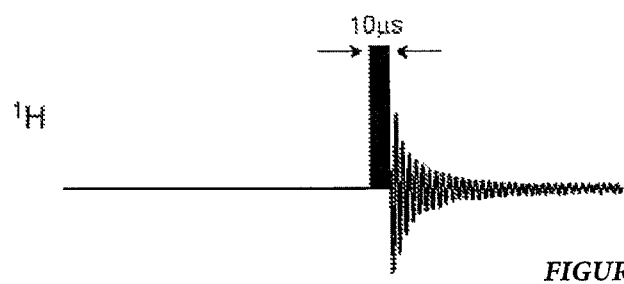
FIGS. 7A-7C provide exemplary RF pulse sequences that may be used for conducting NMR analyzes according to specific embodiments.
Figure 7B:
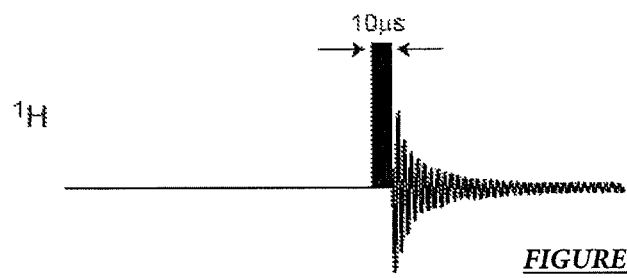
Figure 7C:
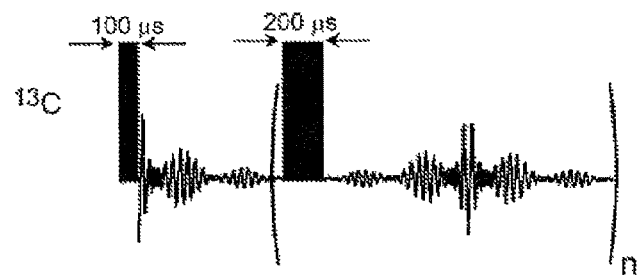

According to specific embodiments, spectra are collecting by pulsing the external frequency reference sample and the detection sample in quick succession. As described below, this may require an RF pulse frequency adjustment for the external frequency reference. Thus, according to specific embodiments, the method proceeds by repeating the sequence (1) pulse the external reference (e.g., $^{19}$F) and save; (2) change the frequency or pulse shape and pulse the isotope of detection (e.g., $^1$H) and save. More than one external frequency references and more than one detection isotope samples may be used. The sequence may be repeated 50, 100 times or more and block averaged as described above. Generally a Fourier Transform (FT) is performed on the reference (e.g., $^{19}$F) and sample ($^1$H). The reference frequencies (e.g., $^{19}$F) are compared with the signal to eliminate or reduce the effect of the magnetic field drift. FIG. 6 illustrates two RF pulses and two received precession signals as an example of one system according to specific embodiments.

In some embodiments of the method, the analysis is on a qualitative level, e.g., are the NMR peaks of interest present or absent. In other embodiments, the analysis is quantitative; the selected peaks are integrated and compared to a standard peak intensity, thereby providing a quantitative analysis of the selected components of the sealed container. In some situations, the NMR resonances generated by the component of interest are sharp, facilitating the optional integration process. The integration can be performed using a software program provided with the spectrometer operational software, or it can be performed the old-fashioned way, by printing the spectra, cutting out the peaks of interest, and weighing the paper scraps.

NMR for Characterizing Substances in Radio Shielding Containers

Conventional high resolution nuclear magnetic resonance (NMR) spectroscopy and magnetic resonance imaging (MRI) can be used to study samples in non-metal, diamagnetic, non-conducting containers and to provide a chemical characterization or identification of at least some components of those samples, as discussed in the above referenced patents. High resolution NMR has not, however, been effectively applied to metal or other radio shielding containers. This is largely due to shielding of the radio frequency (RF) signal in broadcast and received directions caused by metal containers. This shielding (or attenuation) is sometimes expressed as the applied RF penetration depth (or skin depth) d. Skin depth d generally indicates how far radio waves penetrate into metal under various power/frequency conditions. As is well understood in the art at higher RF frequencies the skin depth is smaller, thus reducing the amount of signal that can be transmitted through the metal.

As an example, for conventional high resolution $^1$H NMR spectroscopy (at magnetic field strengths providing Larmor frequencies exceeding 300 MHz ($\lambda$=1 m), the skin depth for aluminum, (an example of a common stream-of-commerce metal container material) is d<5 μm. This means that the RF field inside of, for example, standard aluminum beverage cans with about 100 μm wall thickness will generally be reduced by more than 150 dB compared to the RF field applied outside of the container. This reduction occurs in both directions, e.g., in the broadcast applied RF signal, which is used to stimulate NMR transitions, and in the received free precession RF signals. This RF field strength reduction in both directions generally precludes the routine NMR investigation of samples in metal containers both because the reduced RF amplitude applied to the sample in the container generally does not sufficiently stimulate NMR transitions and because the associated RF free precession signals received outside the container are scaled down below detection levels (e.g., below the noise level of the detecting instrument or apparatus or system).

According to further specific embodiments, systems and methods as described herein obtain chemically resolved $^1$H NMR spectra from materials inside standard aluminum beverage containers (e.g., aluminum or other metallic or non-metallic cans, jars, boxes, or bottles) or various other containers or containment or packaging containing metal or other radio attenuating substances in the packaging using a number of novel approaches. In specific embodiments, one or more issues determined through investigation to hamper the use of NMR for metal or other radio shielded containers are addressed and overcome.

For standard, non-metal containers sensitivity or detection ability is generally directly controlled by the power or size of the applied static magnetic field via the Boltzmann factor. This factor increases with increased magnetic field strength and increased RF operating frequency. This suggests that better NMR sensitivity can be realized at increased magnetic field strength. As will be understood in the art, the resonant frequency of the target molecules, e.g., $^1$H is proportional to the strength of the magnetic field. This resonant frequency determines the desired applied RF.

When metal cans or containers are examined, however, NMR sensitivity is also a function of the RF penetrating skin depth d. RF shielding reduces with increased magnetic field strength, and thus the penetrating skin depth d increases with increased magnetic field strength. However, as is well understood in the art, penetrating skin depth d decreases with increased RF frequency. Combining the Boltzmann factor with the RF shielding effect has been determined according to specific embodiments to indicate that the NMR sensitivity for a liquid in a metal can will be a peaked function of frequency.

Figure 2:
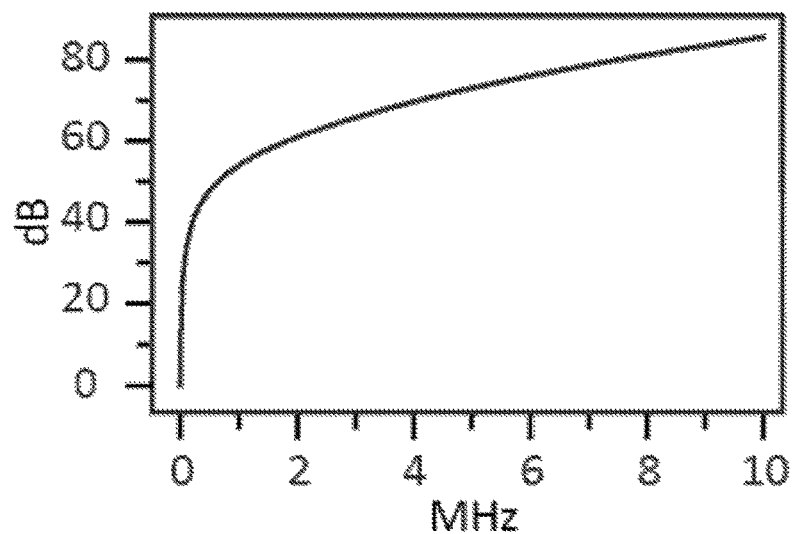
FIG. 2 illustrates the shielding effectiveness (SE) in decibels (db) as a function of radio frequency for a 7 cm diameter aluminum cylinder with a 100 μm thick wall calculated from the analytical result shown in Eq. (5) according to specific embodiments.

It has been determined by the inventors using techniques provided herein that this sensitivity maximum for the RF frequency is in the 4-6 MHz frequency range for stream of commerce aluminum cans with about 100 μm wall thickness. Other frequencies in ranges of about 2 MHz to about 10 MHz may be used, particularly when dealing with different container wall thicknesses or materials or different RF shielding properties. FIG. 2 illustrates the shielding effectiveness (SE) in decibels (db) as a function of radio frequency for a 7 cm diameter aluminum cylinder with a 100 μm thick wall calculated from the analytical result shown in Eq. (5) according to specific embodiments.

Figure 3:
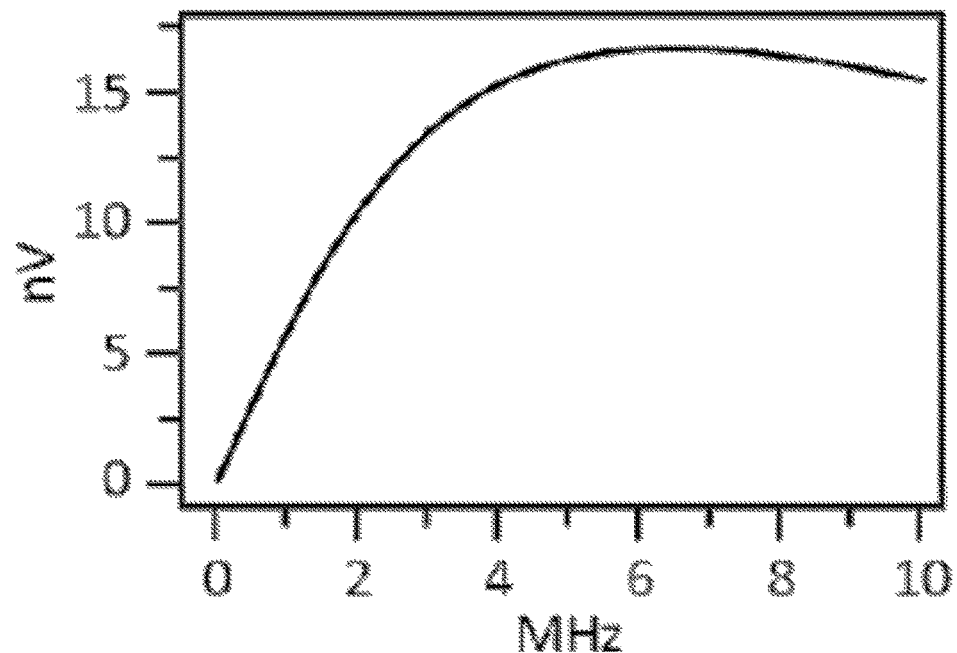
FIG. 3 illustrates the NMR sensitivity expressed as Faraday source voltage ($V_{metal}$ or nV) calculated from Eq. (4) with the metal shield as a function of radio frequency (RF) according to specific embodiments.

The maximum of this function of combining the Boltzmann factor with the RF shielding effect of frequency for aluminum cans with about 100 μm wall thickness is in the 4-6 MHz range as discussed in detail further below. At this reduced frequency of the RF, (e.g., 4-6 MHz, or $\lambda$ of about 75 to 50 meters), the penetrating skin depth d increases to about 50 μm and the far field reduction in RF levels is expected to be 20-40 dB which indicates RF amplitudes a factor of 10-100 lower than encountered in a normal NMR detection. FIG. 3 illustrates the NMR sensitivity expressed as Faraday source voltage (Vmetal or nV) calculated from Eq. (4) with the metal shield as a function of radio frequency (RF) according to specific embodiments. In this particular example setup, the 7 cm diameter, $\eta$=5 turn solenoid RF coil enclosing a 7 cm diameter aluminum cylinder with a 100 μm thick wall containing water provides $\xi=0.8$ and $V_{NMR}=47.2$ µV in the absence of the metal shield, where nV indicates the detected signal.

The distinction between far field vs. near field effects and modeling is known in the art. It is related to the wavelength ($\lambda$) of the applied RF. Generally, when that wavelength is much much greater than the size of the object of interest (e.g., the object being subject to the field), near field effects dominate and a near field model is used. If the object is much much smaller than the wavelength of the applied RF, far field effects dominate and a far field model is used.

While prior investigations have suggested that RF frequencies, to penetrate conducting containers, would need to be so low as to provide little or no signal resolution or chemical detection, according to specific embodiments, it has been determined that that as the RF frequency is reduced, there should be a change in the analysis approach and assumptions previously made (e.g., the mathematical description) regarding how RF penetrates metal. At common high frequencies, where standard high-resolution NMR typically operates, the general mathematical description approaches a far field model while at lower frequencies selected according to specific embodiments a near field analysis approach has been demonstrated to be more useful. Specifically and for example, a standard beverage container may be roughly 0.15 meters long, and a standard milk or other product can or bag or container may be up to about 0.5 meters long or longer. For RF higher than 300 MHz, ($\lambda<1$ m) and for RF lower than 4 MHz, $\lambda>100$ m.

Because of this, according to specific embodiments, it has been determined that the high frequency far field analysis approach of only using the penetrating skin depth d to describe how radio waves are affected by metal shields is not appropriate at lower frequencies. According to specific embodiments, apparatus and methods as described herein use an RF signal frequency that is more accurately characterized by the near field model. According to specific embodiments, at RF of around 3-10 MHz, or around 4-6 MHz, with $\lambda>$about 100 m when examining a container as discussed herein, the near field model is better at describing how the radio waves are affected by metal shields. As a result, according to specific embodiments, a lower static magnetic field is selected for NMR.

Prior research in electromagnetic field testing has determined in part how radio waves interact with metal bodies in the near field. From the point of view of NMR spectroscopy in metal containers at low frequency according to specific embodiments it has been found that the RF shielding or attenuation by the metal shield in most cases is less than previously predicted or expected based solely on the far field model. Thus, according to specific embodiments, systems or methods as described herein use a lower but mid-range frequency RF signal to perform NMR. This provides the ability to examine contents of conducting containers and also provides the ability to use lower static magnetic field strength in some instances.

Some previous work has studied using extremely low frequency NMR to examine the contents of generally large or very large metal containers. At these frequencies, however, there is no resolution of individual chemicals and thus such approaches are not useful for chemical signal detection.

Another issue that arises is that the RF field inside of the can is generally substantially reduced in amplitude in comparison to any RF field of any amplitude or shape applied to the outside of the can. From the point of view of pulsed NMR spectroscopy, this means that although high power RF pulses are applied to the outside of the can, the RF amplitude inside of the can is generally in the very low power range.

According to specific embodiments, systems or methods as described herein do not use the square, constant amplitude and frequency RF pulses (e.g., as shown in FIG. 15) commonly used for example in high resolution liquid state NMR because these do not effectively initiate broadband free precession signals that can be detected outside of the metal container.

Shaped and Adiabatic Pulses

Thus, according to specific embodiments, a generally high power (e.g. 0.5-1 kilowatt, 1-1.5 kilowatt, or any high power source) shaped RF pulses, in some ways similar to the family of broadband frequency and amplitude modulated pulses referred to as adiabatic pulses, are applied to the outside of a metal or RF shielding or other container for which it is desired to analyze the inside contents. The attenuation of the RF amplitude by the metal container then presents a low power broadband excitation pulse to the container contents. This low power broadband excitation pulse causes large free precession signals from the contents of the container, which are then, according to specific embodiments, detected outside the container.

Adiabatic pulses are pulses of various shapes, characterized by modulation of frequency and amplitude generally with a rate of change that causes a more gradual perturbation of the alignment of the nuclear spins than standard square pulses. Adiabatic type pulses at low power have been used in various NMR applications. See, for example, The Return of the Frequency Sweep: Designing Adiabatic Pulses for Contemporary NMR, Advances in Magnetic Resonance Michael Garwood, Lance DelaBarre, Center for Magnetic Resonance Research and Department of Radiology, University of Minnesota, Minneapolis, Minn., 55455, and Tannús et al., NMR IN BIOMEDICINE, VOL. 10, p. 423-434 (1997). While use of low power adiabatic pulses in various NMR applications has been known for decades, use of these pulses today remains generally in niche areas such as portable NMR devices. While adiabatic pulses have been used in the present investigation, other RF pulses that act on nuclei in a similar way (e.g., various soliton pulses) can also be used according to specific embodiments.

Specific embodiments of methods and systems as described herein are configured to account for the effect of an RF shielding container on broadcast and received RF amplitudes as discussed in more detail below. According to specific embodiments, results have shown that use of high powered adiabatic pulses can accomplish chemically resolved or chemically informative NMR spectroscopy of substances in metal containers.

Shielding Effectiveness

Modern embodiments of NMR spectroscopy typically involve the broadcast of short high power micro-second (µs) time scale RF pulses followed by the reception of longer seconds (s) time scale low power RF free precession signals. During broadcast, high voltage RF pulses are applied to a tuned LC tank circuit. The tank circuit impedance provides a RF current that ultimately results in a RF magnetic field with amplitude $B_1^{app}$ that rotates the equilibrium magnetization $M_o$ away from the large applied static magnetic field $B_o$ to the perpendicular transverse plane.

At high temperature, the equilibrium magnetization $M_o$ in terms of the spin density N, the gyromagnetic ratio $\gamma$, the Planck constant $\hbar$, the Boltzmann constant K, the temperature T, and the Larmor frequency $\omega_0$ is:

$$M_0 = \frac{N\gamma\hbar^2\omega_0}{2KT} \quad (1)$$

Following the RF broadcast pulse, the magnetization begins to precess and, according to the reciprocity principle and Faraday's law, induces an EMF or voltage $V_{NMR}$ in the LC tank circuit. The magnitude of this oscillating voltage is:

$$V_{NMR} = 4\pi\eta\xi A\omega_0 M_0 = \frac{4\pi\eta\xi AN\gamma\hbar^2\omega_0^2}{2KT}, \quad (2)$$

with standard symbols, e.g., where $\eta$ is the number of turns in the inductor L, $\xi$ is the geometric filling factor of the sample in the coil, A is the cross sectional area of the coil, and the definition of $M_0$ in Eq. (1) has been applied.

The size of the broadcast field $B^{app}$ and the received voltage $V_{NMR}$ in a standard NMR analysis performed on non-metal, non-conducting sample containers changes when operating on metal, non-ferrous cans. The reduction in both $B^{app}$ and $V_{NMR}$ by the metal container is the same and in these equations is described in terms of the shielding effectiveness (SE) as:

$$B_1^{metal} = 10^{-SE/20} B_1^{app} | \quad (3)$$

and $$V_{metal} = 10^{-SE/20} V_{NMR} \quad (4).$$

The SE for the experiments reported here involving a solenoid RF coil enclosing a standard 12 oz aluminum container along the x direction of the laboratory frame where the z axis is defined by the direction of the static magnetic field.

According to specific embodiments, it has been determined using finite element numerical modeling of a closed, cylindrical, 100 µm wall thickness standard aluminum beverage container such as reported here that the SE for an infinitely long conducting metal cylinder as expressed in Eq. 5 is a good analytical approximation for the actual case involving a finite closed metal can or container.

$$SE = -20\log\left[\text{mod}\left(\frac{2i}{(ka)^2}\left(\frac{1}{I_0(\beta)K_2(\alpha) - I_2(\alpha)K_0(\beta)}\right)\right)\right] \quad (5)$$

In Eq. (5) $k^2 = \mu\sigma\omega_0$ is written in terms of the metal permeability $\mu$ and conductivity $\sigma$. The modified Bessel functions $I_0(\beta)$ and $K_2(\alpha)$ are written in terms of the inner a and outer b container radius via the parameters $\alpha = i^{1/2}ka$ and $\beta = i^{1/2}kb$.

Custom Built NMR Probe for Stream of Commerce Metal Beverage Cans

The subsequent experimental section describes an example custom built NMR probe according to specific embodiments that, for example, can accommodate stream of commerce metal beverage cans and similar containers. FIG. 1 is a schematic drawing of an exemplary probe of the present invention showing a metallic container and a reference sample in a single coil NMR probe according to specific embodiments. One specific example custom built NMR probe used an 11.5 cm diameter, 11 turn variable pitch solenoid RF coil tuned to the 4 MHz $^1$H Larmor frequency offered by a 980 G SMIS electromagnet equipped with room temperature shims and having a 15.24 cm pole face separation.

Experimental NMR spectra as discussed herein were obtained using an example custom built NMR spectrometer, in this instance based on a double-resonance Tecmag Redstone pulse programmer.

Results

An analysis of Eqs. (3) and (4) has demonstrated that the primary difference between operation in a metal versus non-metal container from the standpoint of generating and receiving NMR signals is the reduction of RF amplitude by the presence of the conducting metal shield. A key parameter that describes this reduction in the case of a cylindrical metal container in these examples is the shielding effectiveness, SE, as shown in Eq. (5).

FIG. 2 illustrates the shielding effectiveness (SE) in decibels (db) as a function of radio frequency for a 7 cm diameter aluminum cylinder with a 100 µm thick wall calculated from the analytical result shown in Eq. (5) according to specific embodiments. This SE as determined from Eq. (5) is a function of RF for an example 7 cm diameter, 100 µm thick aluminum cylinder. The SE values as illustrated in FIG. 2 can be used in Eq. (4) to determine the effect of the cylindrical aluminum shield on the size of the measured voltage $V_{metal}$ as shown in FIG. 3.

Figure 4:
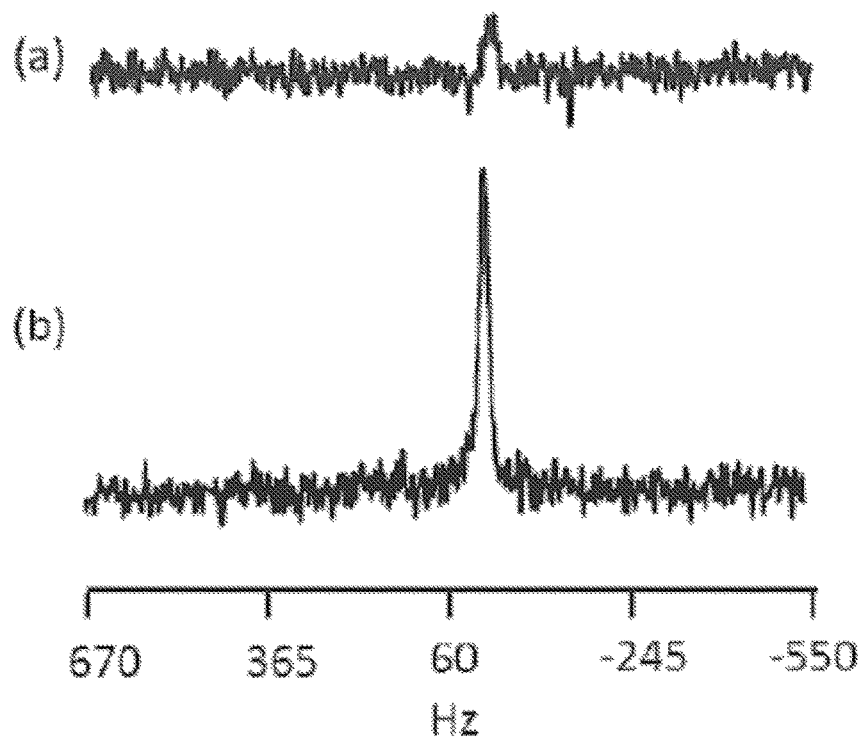
FIG. 4 illustrates a comparison of the $^1H$ NMR spectra at 4 MHz for a cappuccino drink in a standard 8 oz aluminum beverage can. The results in (a) were obtained with a 50 ms long constant amplitude and frequency pulse as would be common in the art while those in (b) were obtained with an amplitude and frequency swept adiabatic pulse according to specific embodiments.

The $^1$H NMR spectra shown in FIG. 4 for a standard 8 oz metal cappuccino container were obtained with a standard constant amplitude and frequency RF pulse in (a) and with a frequency and amplitude modulated adiabatic half soliton pulse in (b). In both spectra, 50 free induction signals were obtained and averaged. The spectrum in (a) was generated with a 50 ms long, constant frequency and amplitude pulse while the spectrum in (b) was obtained with the half soliton pulse by sweeping the frequency from 12.5 Hz below resonance to resonance in a hyperbolic tangent fashion in 100 ms while increasing the amplitude in a hyperbolic secant fashion from nearly zero to the same amplitude used in (a) in (b). The enhancement observed by operating with a shaped pulse is about an order of magnitude.

In specific embodiments, experiments were run using solvents as received as indicated below as a proof-of-concept sample substance. The example experimental results discussed here were accomplished using commonly available stream-of-commerce, non-ferrous metal containers as examples, a number of which are referenced below. Examples described herein in which mixtures of pure solvents are reported used 24 oz screw-cap Monster® drink cans.

Figure 5:
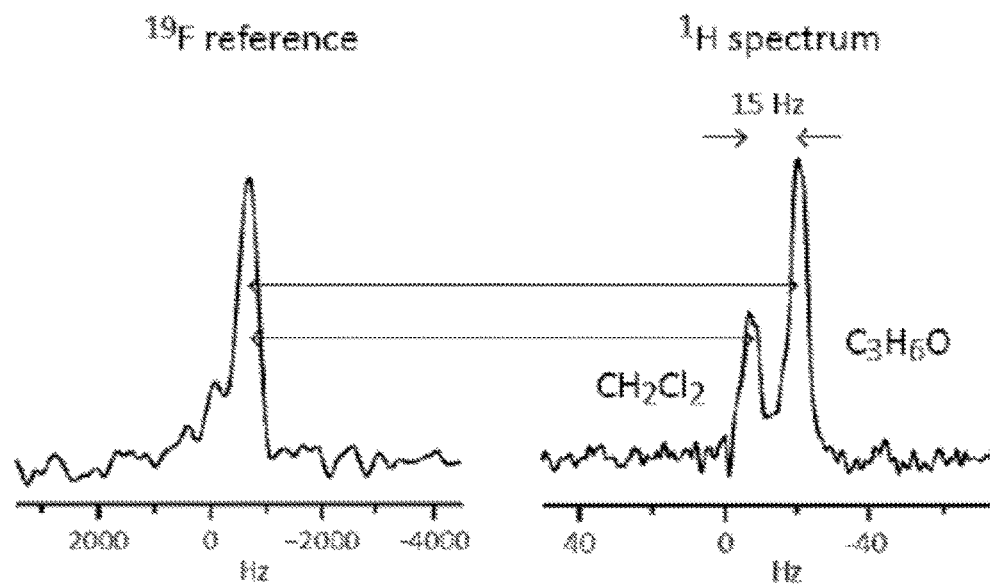
FIG. 5 illustrates $^1H$ NMR spectrum at 4 MHz for a mixture of acetone ($C_3H_6O$) and methylene chloride ($CH_2Cl_2$) in a 12 oz aluminum can used for experimental proof of concept according to specific embodiments.

FIG. 5 demonstrates the chemical sensitivity and frequency referencing capability of the experimental setup. Here the adiabatic approach was used to record the $^1$H spectrum for a mixture of methylene chloride and acetone. As described in the text, a sample of perfluorocyclohexane is mounted inside of the RF coil to provide a frequency reference.

Thus, In the case of standard 12 oz stream-of-commerce cylindrical metal cans, the amplitude reduction factor is related to the SE shown in Eq. (5). This Eq. 5 expression for the SE is appropriate for an infinite cylindrical metal shell housed inside of an infinitely long solenoid RF coil. Although the infinite cylinder does not have end caps like the real stream-of-commerce container, the SE values calculated from Eq. (5) compare very well with results from finite element modeling and the SE expression for a spherical shell. Spherical samples and other closed samples were examined as part of the analysis. This observation suggests that the end caps of a closed conducting metal cylinder contribute very little to the SE value for a real metal container. Moreover it is contributions from the cylindrical shell (e.g., the container wall) that dominate the SE value. The end caps contribute very little to the overall SE because the cylindrical metal container wrapped with a solenoid RF coil has the RF field directed into the end cap. Given Maxwell's equations in conducting media, the boundary conditions, and the geometry, the applied RF field cannot establish an eddy current on the end cap surface, and there is minimal to no contribution to the SE value.

On the other hand, the cylindrical surface (e.g., the outside of a metal can, bottle, or other container) is perfectly poised to support eddy current formation, which largely is the cause of the shielding of the RF signal from the contents of the container. In fact, the applied RF field generates an eddy current that wraps around the container, in a direction opposing the current flow in the solenoid RF coil. The consequence of these opposing directions is that the eddy current establishes a field inside of the can in the opposite direction of the applied RF field. It is the difference between the applied RF field and the eddy current generated RF field inside of the metal container that ultimately yields the SE value that relates $B^{app}$ and $V_{NMR}$ to $B1^{metal}$ and $V_{metal}$, in Eqs. (3) and (4).

The amount of attenuation of the applied RF pulse by the metal shield depends on the type of metal and its thickness according to Eq. (5). Because one application according to specific embodiments involves standard, stream-of-commerce, metal, non-ferrous cans, the SE was explored as a function of frequency for a 7 cm inner diameter, 100 µm thick aluminum can.

SE values calculated from Eq. (5) and shown in FIG. 2 for three wall thicknesses indicate that 50 dB≤SE≤80 dB at readily available 1 MHz≤$\omega_0/2\pi$≤10 MHz Larmor frequencies. These results suggest that in this frequency range $B^{app}$ is scaled by roughly a factor of 1,000. This means that a standard 5 µs long $\pi/2$ RF pulse applied to $^1H$ nuclei where $B^{app}$=11.8 G translates into a $B_1^{metal}$=11.8 mG field when the metal cylinder is present. In order to have the same $\pi/2$ magnetization tip angle with the metal shield, a much longer 5 ms long RF pulse would have to be used.

One can also view the effect of the metal container from the standpoint of voltage. If a 1,000 volt RF pulse yielded the 5 µs, $B^{app}$=11.8 G characteristics, the metal shield produces a reduced field $B_1^{metal}$ that appears as if it were created by a 1 volt RF pulse. Regardless of how the effect of the metal container is considered, the consequence is the same from the point of view of the spins inside of the metal container. Although high power RF pulses are applied, the spins inside of the metal container generally experience weak or very weak RF fields.

Thus, according to specific embodiments, systems or methods such as described herein apply very high power shaped RF pulses (such as adiabatic pulses at 0.5 or 1 kW or higher) to samples in metal containers recognizing that in low RF field situations adiabatic RF pulses can be used to improve the sensitivity of NMR spectroscopy by increasing the pulse excitation bandwidth.

The metal cylindrical shield also attenuates the free precession signal amplitude $V_{NMR}$. This effect is captured in FIG. 3 for the same cylindrical shell used in FIG. 2. The shape of the curve in FIG. 3 corresponds to the interplay of Boltzmann magnetization that increases with $\omega_0{}^2$ and the steep drop off in $10^{-SE/20}$ with increasing $\omega_0$. The results shown in FIG. 2 suggest that frequencies in roughly the 4 MHz<$\omega_0/2\pi$<7 MHz range will be most sensitive since most stream-of-commerce metal containers have wall thicknesses between 75 µm and 120 µm. According to other embodiments, that RF frequencies in the range of about 3 to 10 MHz provide the most sensitivity in some of the specific applications described herein.

Using the demonstrations shown, specific embodiments apply a shaped 4-5 MHz RF pulses (e.g., such as, for example, those designed to work in low RF power situations) at high RF power to achieve better detection results when using samples in metal containers with a approximately 50-100 µm wall thickness.

FIG. 4 compares the results obtained from a metal stream-of-commerce container using a standard, constant frequency, constant amplitude RF pulse in (a) and an adiabatic, frequency swept, amplitude modulated RF pulse in (b). In both cases the same number of scans (e.g., 50) were averaged to produce the spectra. The improvement of the received signal strength by operation with a high power shaped pulse is close to an order of magnitude, as calculated from the ratio of the integrated area of the spectrum in (b) to the one in (a).

Several examples of adiabatic RF pulses can be used according to specific embodiments. For example, half soliton hyperbolic pulses used to generate FIG. 4(b) in addition to linear and non-linear frequency and amplitude sweeps and mixtures of constant and variable amplitude and frequency changes.

In specific example experimental systems, the best experimental results were obtained by operation with adiabatic hyperbolic half soliton pulses. However, the best pulse types or characteristics may vary with different specific configurations according to specific embodiments.

Although the optimum 4 MHz $^1H$ Larmor frequency is low and the entire associated $^1H$ chemical shift range is 40 Hz, in experimental embodiments, the magnetic field shims as will be generally understood in the art provided chemical sensitivity as shown in FIG. 5 for a mixture of methylene chloride and acetone.

External Frequency Reference

Another issue that must be considered, for example when trying to detect NMR fingerprints of substances in metal cans, is frequency referencing. In standard high resolution $^1H$ NMR spectroscopy, frequency referencing can be accomplished by spiking the sample with a non-reactive compound like tetramethylsilane. This approach will not work for sealed metal cans as a reference compound cannot be added to a sealed metal container and any protonated reference compound will generally interfere with the $^1H$ NMR spectrum of the container contents because the entire 10 ppm $^1H$ chemical shift range collapses from 4 KHz at the standard high 400 MHz Larmor frequency to 40 Hz at the reduced (e.g., 4 MHz, or 2-7 MHz) frequency generally used according to specific embodiments.

In the wine bottle applications mentioned above, the internal substance of ethanol can be used effectively as a built-in spike, as this molecule is always be present in substantial quantities in wine.

According to specific embodiments, these problems with signal referencing are circumvented by using an external reference, such as an external heteronuclear frequency reference. In one example, a sample of perfluorocyclohexane is used to reference the field and frequency via $^{19}F$ NMR spectroscopy. According to specific embodiments, a tank circuit used to obtain $^1H$ NMR spectra at 4 MHz (and nearby frequencies) can also be used to detect the $^{19}F$ reference frequency as it is still in the hard pulse excitation bandwidth of the circuit, which in one example is roughly 350 kHz lower at 3.65 MHz. The $^{19}$F was specifically chosen for use at this frequency.

According to further specific embodiments, the identity of various compounds can be determined with reference to the external $^{19}$F standard as shown in FIG. 5. The 3.75 ppm separation of the peaks indicates that at least these two compounds can be identified by $^1$H NMR spectroscopy at a 4 MHz Larmor frequency. The ultimate resolution of the analysis can be obtained from the full width at half maximum of the separate peaks. According to FIG. 5, the line width is 1.6 ppm, meaning that chemically shifted peaks below and above this difference will coalesce and separate respectively.

While FIG. 5 shows two distinct peaks, one use of the invention is the screening of complex chemical mixtures, for example to determine if the contents of a sealed container is the expected mixture or to determine if one or more contraband or containment substances are present. According to specific embodiments, the NMR spectrum at a moderate 980 G applied static magnetic field be either one unresolved symmetric or asymmetric peak having a center of gravity frequency that represents the population weighted average of all of the chemical compounds in the sample. Although this overall shift is not enough to identify all of the components in the liquid, it is unique for the liquid, and along with other NMR parameters such as the spin lattice relaxation, the spin spin relaxation, diffusion constants, and J couplings, this overall shift is enough to identify the liquid by comparison to a database or other references as will be understood in the art.

For example, most stream of commerce beverages will have similar peaks. The presence of a contraband liquid in a stream of commerce beverage container will cause the signal position and shape to change sufficiently to be detected by methods and systems as described herein.

In specific example embodiments, spectral referencing of the $^1$H NMR signal was accomplished using the $^{19}$F NMR response from pure perfluorocyclohexane held in a separate small glass container mounted inside of the RF coil immediately below the metal beverage container. According to specific embodiments, the approximately 350 kHz difference in Larmor frequency between $^1$H and $^{19}$F nuclei at the applied 980 G static magnetic field allows for external spectral referencing with just one transmitter and one RF tank circuit.

Other external references could be used including protonated samples, with an additive in them, or any other compound that is sensitive.

In an example system, the RF transmitter is shifted to the $^{19}$F Larmor frequency (which in this case is 3.75 MHz), an RF pulse is applied (generally a standard square pulse rather than an adiabatic pulse as the external reference is generally not in a metal container), and the free induction signal is recorded. Immediately following signal acquisition, the RF transmitter is shifted back to the $^1$H Larmor frequency and either a hard rectangular RF pulse (for standard high resolution NMR) or shaped adiabatic RF pulse is applied followed by acquisition of the $^1$H free induction signal. In this way, each $^1$H free induction signal is reference to the $^{19}$F frequency, a feature that permits efficient block averaging for $^1$H signal amplification. In these examples, experiments are performed without a field frequency lock.

NMR Probes

The present invention also provides NMR probes for use in the methods described herein. The NMR probes of the present invention are configured to position a portion of a sealed container within an NMR spectrometer, thus avoiding the need to violate the seal on the container in order to analyze the contents. The probes typically comprise a body structure having a cavity disposed at a first end of the body structure, a first RF coil positioned proximal to the cavity and the portion of the sealed container; and a tuning capacitor coupled to the RF coil and to a length of coaxial cable configured for connection to the NMR spectrometer. In an alternate embodiment, the cavity is disposed in a middle region of the body structure, rather than proximal to the end of the probe.

The probes of the present invention can be used to detect any desired nuclei capable of generating a nuclear magnetic resonance and having adequate chemical shift dispersion between selected contaminant and/or sample signals. Thus, the probes of the present invention include, but are not limited to, $^1$H probes, $^2$H probes, $^{13}$C probes, $^{17}$O probes, and the like. Furthermore, the probes of the present invention can be single frequency or dual frequency probes (e.g., a $^1$H/$^{13}$C probe).

The body of the probe is typically composed of material having a low magnetic susceptibility to reduce and/or prevent distortion of the static magnetic field when the probe is positioned in the spectrometer. Exemplary materials used in the manufacture of the body structure of the probe (or portions thereof) include, but are not limited to stainless steel, aluminum, glass, ceramic, and plastics such as Teflon (polytetrafluoroethene), Kel-F (polychlorotrifluoroetene), and PVC (polyvinylchloride).

Figure 8:
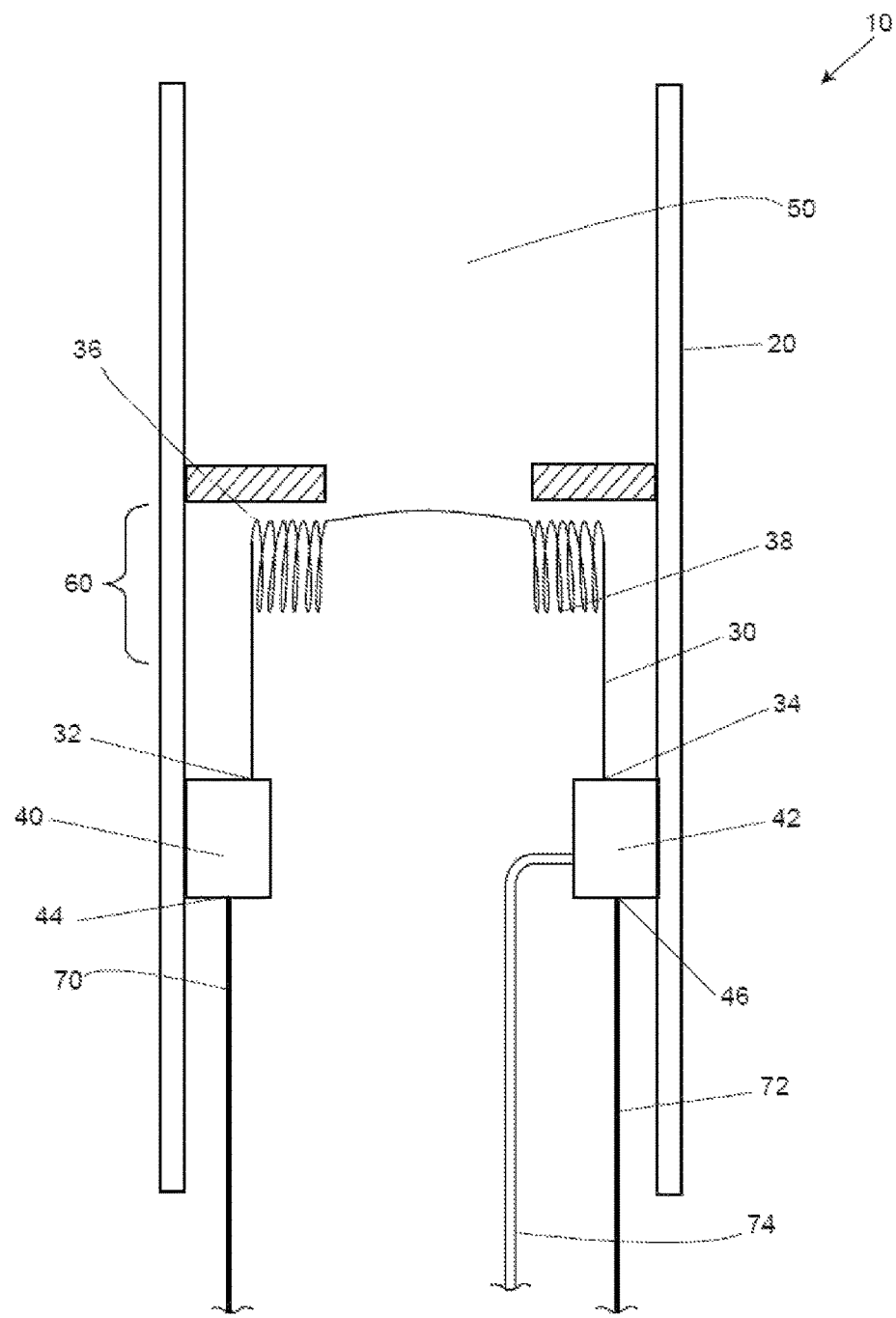
FIG. 8 depicts a view of an exemplary probe, showing a space for receiving a sealed container within the data collection region according to specific embodiments.
Figure 9:
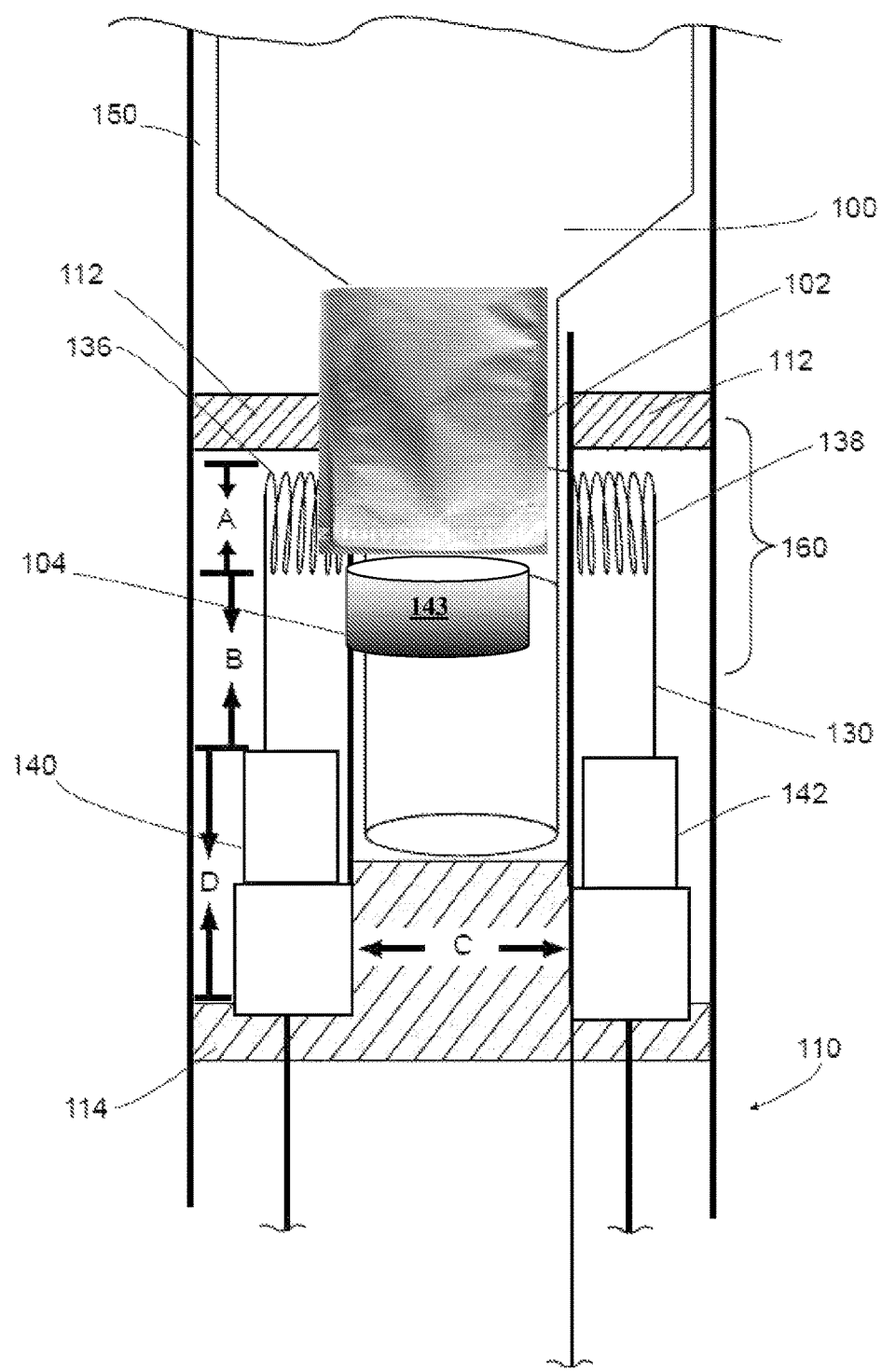
FIG. 9 depicts an expanded view of an exemplary probe, showing the placement of a sealed container within the data collection region according to specific embodiments.
Figure 10A:
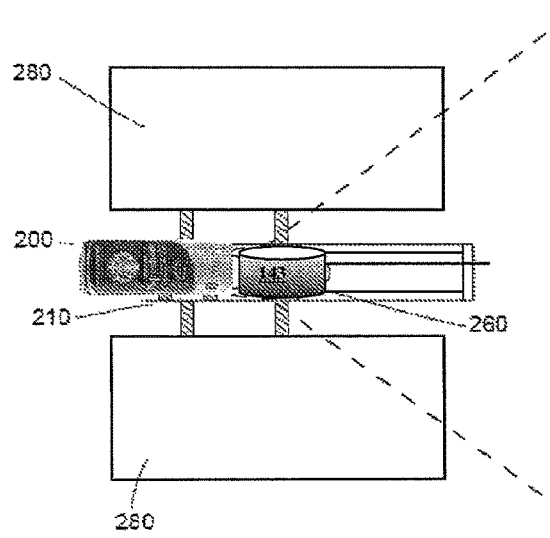
FIGS. 10A-10B represent one embodiment of the systems of the present invention, depicting an experimental setup used to obtain an NMR spectrum of a full, intact container. (A) provides a schematic depicting the placement of the sealed container (e.g., a metallic food or beverage container) and an NMR probe within the body structure of an NMR spectrometer. (B) shows an expanded view of the probe, depicting the positioning of the selected portion of the container with the RF coils of the probe, and indicating that the NMR probe head is capable of housing an entire container of interest.
Figure 10B:
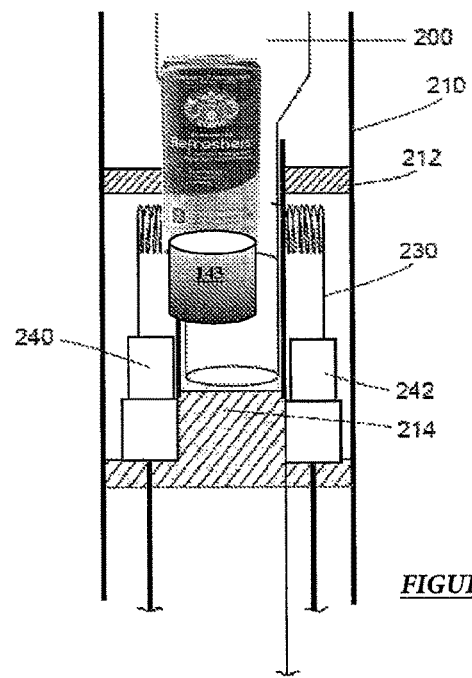
Figure 11A:
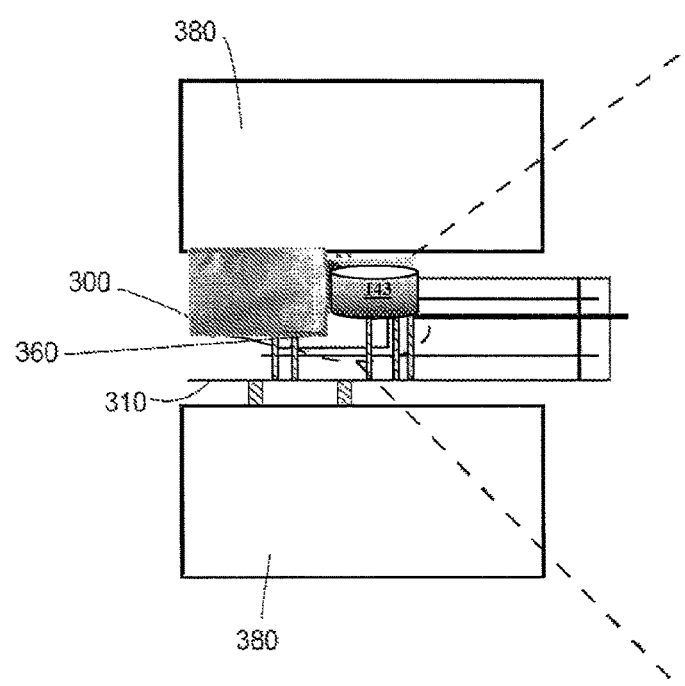
FIGS. 11A-11B depict an alternative embodiment of the systems of the present invention, showing the placement of the body of the sealed container within the NMR probe. (B) shows an expanded view of the probe, depicting the positioning of the body of the container within the sample measurement region of the probe.
Figure 11B:
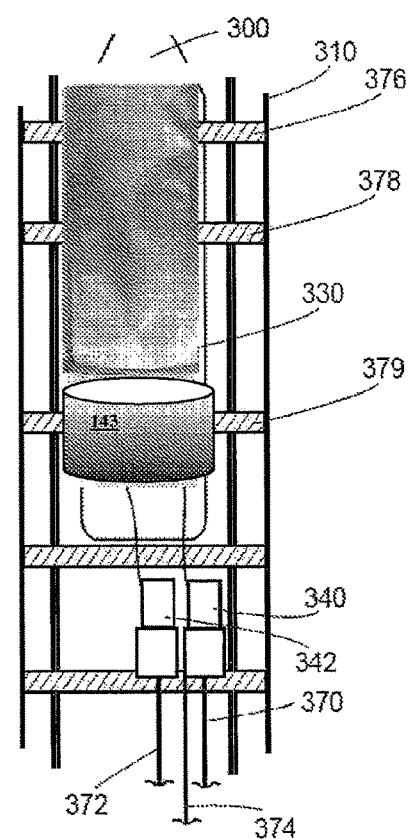

The body structure of the probe has a cavity that is configured to accept a portion of the sealed container, such that a portion of the container is positioned within the data collection region of the probe. Thus, the sample cavity is greater than that typically employed in an probe configured for NMR tubes. The overall dimensions of the probe optionally range from about 600 mm to 800 mm in length, preferably about 700 mm. The outer diameter of the probe ranges in size from 100 mm to 150 mm in diameter, although an outer diameter of up to 310 mm is possible with the current magnet embodiment. FIG. 8 depicts a view of an exemplary probe, showing a space for receiving a sealed container within the data collection region according to specific embodiments. FIG. 9 depicts an expanded view of an exemplary probe, showing the placement of a sealed container within the data collection region according to specific embodiments. FIG. 10 panels A and B represent one embodiment of the systems of the present invention, depicting an experimental setup used to obtain an NMR spectrum of a full, intact container. (A) provides a schematic depicting the placement of the sealed container (e.g., a metallic food or beverage container) and an NMR probe within the body structure of an NMR spectrometer. (B) shows an expanded view of the probe, depicting the positioning of the selected portion of the container with the RF coils of the probe, and indicating that the NMR probe head is capable of housing an entire container of interest. FIG. 11 panels A and B depict an alternative embodiment of the systems of the present invention, showing the placement of the body of the sealed container within the NMR probe. (B) shows an expanded view of the probe, depicting the positioning of the body of the container within the sample measurement region of the probe. The size of the cavity portion of the probe will depend upon the sealed container to be analyzed; for a probe configured to accept a neck portion of a bottle, e.g., a wine bottle, dairy bottle, or other metallic bottle, the cavity portion of the probe will typically range from 34 mm to 85 mm in diameter. Larger cavities able to encompass a wider portion of a container, such as the base and/or body of a can, box, or bottle (e.g., about 100-150 mm in diameter), are also contemplated.

The cavity is configured to hold the sealed container in position through the use of, for example, one or more PVC positioning rings. In one embodiment, the cavity extends from one end of the probe to the data collection region, for insertion of the sealed container from the open end. In an alternate embodiment, the cavity is enclosed within the body structure, and accessed by an opening in the side of the body structure.

The first RF coil is positioned in the body structure of the probe, proximal to the cavity (and the selected region of the sealed container inserted therein). Optionally, the first RF coil functions as both the transmitting coil and the receiving coil. In one embodiment, the first RF coil is a split solenoid coil. An exemplary split solenoid coil is 12 gauge copper wire wound in a 1 cm diameter spiral, the first coil portion having 4 turns of the copper wire, and coupled (via a connecting portion of the wire) to a second coil portion having another 4 turns of copper wire. The first coil portion is positioned on one side of the cavity, while the second coil portion is positioned on an opposite side of the cavity; the connecting wire runs between the two portions without crossing the cavity itself (e.g., along the circumference of the cavity). Preferably, the second coil portioned is aligned along a same axis as the first coil portion.

In another embodiment, the RF coil circumscribes the cavity (e.g., the walls of the body structure defining the cavity act as a former around which the RF coil is wound.) In a further embodiment of the probe, the first RF coil comprises a birdcage-style coil. Such a configuration of coil portions is described in, for example, Hayes et al. (1985) "An efficient, highly homogeneous radiofrequency coil for whole-body NMR imaging at 1.5 T" *J. Magn. Reson.* 63:622-628.

The probes of the present invention also include one or more tuning capacitors. The tuning capacitor is coupled at a first position to the first RF coil, and coupled at a second position to a length of coaxial cable configured for connection to the NMR spectrometer. In one embodiment, the tuning capacitor is a non-magnetic 0-10 picofarad high power RF capacitor.

FIG. 8 depicts a view of an exemplary probe, showing a space for receiving a sealed container within the data collection region according to specific embodiments. Probe 10 comprises body structure 20, first RF (radiofrequency) coil 30; and tuning capacitors 40 and 42. Body structure 20 has opening or cavity 50 disposed at one end for receiving the sealed container (not shown).

A portion of cavity 50 extends into data collection region 60 of probe 10. First RF coil 30 is attached to capacitor 40 at a first end 32 and attached to capacitor 42 at a second end 34, and is positioned proximal to cavity 50 such that coil portions 36 and 38 are situated to either side of data collection region 60.

Tuning capacitors 40 and 42 are also coupled at second positions 44 and 46 to coaxial cables 70 and 72, which are configured for connection to the NMR spectrometer (not shown). In addition, tuning capacitor 42 is coupled at a third position to RF in/out coaxial cable 74, which provides the radiofrequency signal for NMR spectrum generation.

FIG. 9 depicts an expanded view of an exemplary probe, showing the placement of a sealed container within the data collection region according to specific embodiments. Exemplary probe 110 as shown, indicates the placement of sealed container 100 (in this example, a bag made partially from aluminum) within the data collection region 160. Each of the figures also shows a container with a reference substance 143 as described herein. Coil portions 136 and 138 of RF coil 130 are approximately of a diameter and configuration to allow placement of the container and extend from the upper surface of tuning capacitors 140 and 142, respectively. Coil portions 136 and 138 are positioned in this example approximately 3.4 cm apart (measurement C) with the intermediate coil portion (represented by dotted line) arcing between the two portions, such that neck portion 102 of sealed container 100 can be positioned between coil portions 136 and 138 for optimal data collection Probe 110 optionally includes positioning ring 112 separating RF coil 130 from the main portion of cavity 150; the aperture in positioning ring 112 allows the selected portion of container 100 to be positioned within data collection region 160 while protecting this region from dust, etc. Optional capacitor stand 114 is positioned on the distal side of tuning capacitors 140 and 142. Capacitors 140 and 142 are approximately 4.5 cm in height; therefore, the distance between a far edge of coil portion 136 and the distal side of capacitor 140 is approximately 9 cm, and the distance between outer edges of positioning ring 112 and capacitor stand 114 is approximately 11 cm.

The probes of the present invention optionally incorporate a second RF coil, preferably positioned distal to the first RF coil. The second RF coil can be employed for a number of purposes. For example, the second RF coil can be used for either transmitting or receiving the RF signal (in embodiments in which the first RF coil does not function as both transmitter and receiver). Alternatively, the second RF coil can be configured for measurement of one or more signals from a calibration sample. In yet another embodiment, the second RF coil $^{13}C$, $^{17}O$, $^{2}H$, provides for selective excitation of a heteronucleus (including, but not limited to, $^{23}Na$, $^{27}Al$, $^{199}Hg$, $^{207}Pb$, and the like).

The probes of the present invention optionally incorporate an external reference sample or a space for holding an external reference sample, for example as shown in FIG. 1.

Optionally, the probe further includes one or more components for tuning and/or impedance matching the RF coil(s) to at least one RF power source at a selected frequency.

The probes of the present invention optionally include one or more additional components which enhance the functioning of the probe. For example, the probe can include components for generating magnetic field gradients, which can be used, for example, for imaging purposes. In some embodiments, the probe includes a calibration fluid sample tube. The optional calibration sample tube is typically positioned within the cavity of the body structure such that the calibration sample is positioned proximal to the selected portion of the sealed container when the container is inserted in the cavity. The calibration tube is generally of the same expected substance as the detection materials and is interrogated at a separate time.

In a further embodiment, the NMR probes of the present invention optionally further include a fluid jacket, reservoir or other mechanism for modulating the temperature of the probe. Exemplary fluid jacket designs for use with the present invention are described in, for example, U.S. Pat. No. 5,530,353 titled "Variable Temperature NMR Probe" (Blanz).

System Components

The NMR spectrometer typically comprises a body structure, a magnet housed within the body structure, a bore proximal to the magnet and configured to receive the NMR probe, and an amplifier configured for coupling to a first position on the NMR probe. Optionally, the magnet is a constant external magnet, a room temperature (RT) magnet, and/or a superconducting magnet. Any NMR spectrometer having a bore capable of receiving the NMR probes can be used in the systems of the present invention. Preferably, the NMR spectrometer is a super wide bore spectrometer. Exemplary spectrometers are available commercially from, for example, Varian (Palo Alto, Calif.; www.varianinc.com) and Bruker (Germany, www.bruker.com). The field strength of the magnet component used in the systems can also vary, ranging from about 600 Gs to about 2000 Gs and is selected as described herein to provide a sufficient detectable precession signal with an RF frequency that has the desired lower frequency properties.

The systems of the present invention include a receiver system configured for electronic communication with the NMR probe. Optionally, the receiver system is incorporated into the body structure of the NMR spectrometer. The receiver system typically comprises a preamplifier configured for coupling to the NMR probe and a detector in communication with the preamplifier. In one embodiment of the systems of the present invention, the receiver includes a passive RF duplexer as well as electronics for signal mixing and digitization (see, for example, Fukushima and Roeder, *Experimental Pulse NMR a Nuts and Bolts Approach*, Addison-Wesley, New York, 1981).

In some embodiments of the present invention, the system includes a mechanism for spinning the sealed container within the NMR probe. Exemplary spinning mechanisms include, but are not limited to air-propelled mechanisms (e.g., air turbines), rotor mechanisms, strap-based mechanisms and the like.

In a preferred embodiment of the present invention, the system also includes a RF power source, for exciting the nuclei within the sealed container.

FIG. 10 panels A and B represent one embodiment of the systems of the present invention, depicting an experimental setup used to obtain an NMR spectrum of a full, intact container. (A) provides a schematic depicting the placement of the sealed container (e.g., a metallic food or beverage container) and an NMR probe within the body structure of an NMR spectrometer. (B) shows an expanded view of the probe, depicting the positioning of the selected portion of the container with the RF coils of the probe, and indicating that the NMR probe head is capable of housing an entire container of interest. The figure illustrates an exemplary system of the present invention depicting the positioning of container 200 within the data collection region 260 of probe 210, which is inserted into magnet 280 of the NMR spectrometer. (B) shows the alignment of container 200 within probe 210 with respect to RF coil 230 and tuning capacitors 240 and 242. Also depicted are optional components positioning ring 212 and capacitor stand 214.

FIG. 11 panels A and B depict an alternative embodiment of the systems of the present invention, showing the placement of the body of the sealed container within the NMR probe. (B) shows an expanded view of the probe, depicting the positioning of the body of the container within the sample measurement region of the probe. The figures depict an alternate positioning of container 300 within the data collection region of probe 310, in which the body of container 300 is inserted into data collection region 360. In (A), probe 310 is inserted into magnet 380 of the NMR spectrometer. (B) shows RF coil 330, tuning capacitors 340 and 342, coaxial cables 370 and 372, and RF in/out cable 374, with respect to the alignment of container 300 within probe 310. Positioning ring 376 centers the sample inside of RF coil 330, which is mounted on PVC positioning rings 378 and 379.

While different nuclei including deuterium ($^2H$), oxygen ($^{17}O$), carbon ($^{13}C$), and hydrogen ($^1H$) can be used as possible candidates for determining levels or presence of various contaminants or components the $^1H$ nucleus is often the best choice due to its superior sensitivity and if there is a sufficient chemical shift difference between the spectrum of a contaminant and the spectra of the expected constituents of the contents of the metallic container.

Airport or Building Security Scanner

Figure 12:
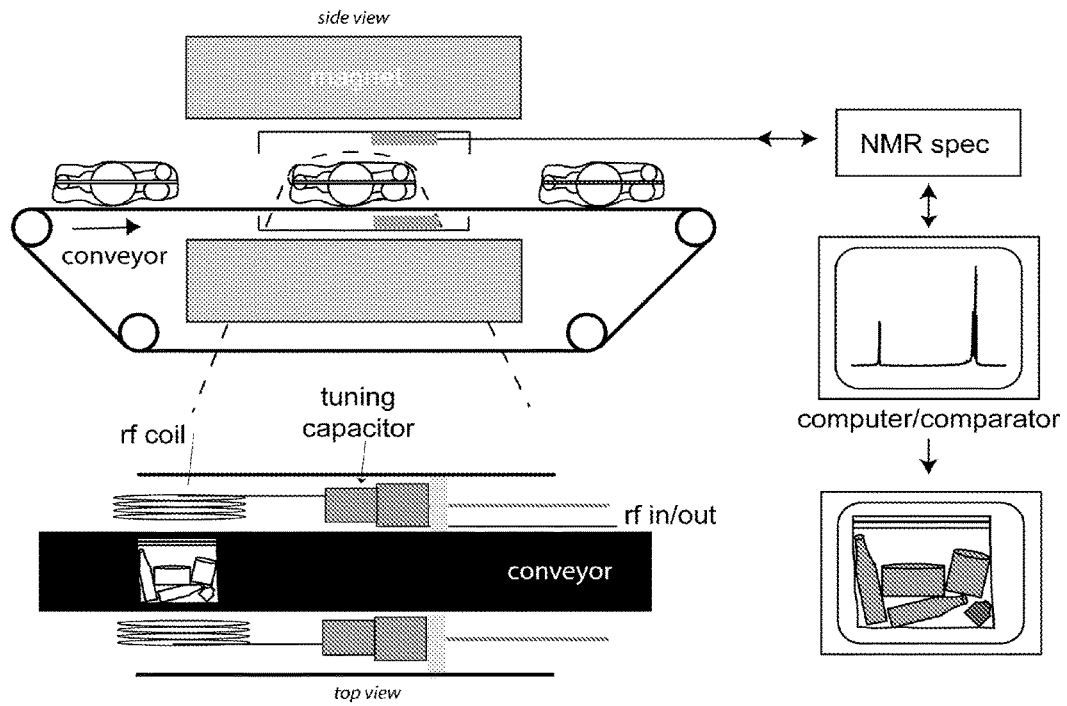
FIG. 12 depicts a security conveyor device including an exemplary probe according to specific embodiments and configured for scanning a bag containing liquids in metallic and/or non metallic containers.
Figure 13:
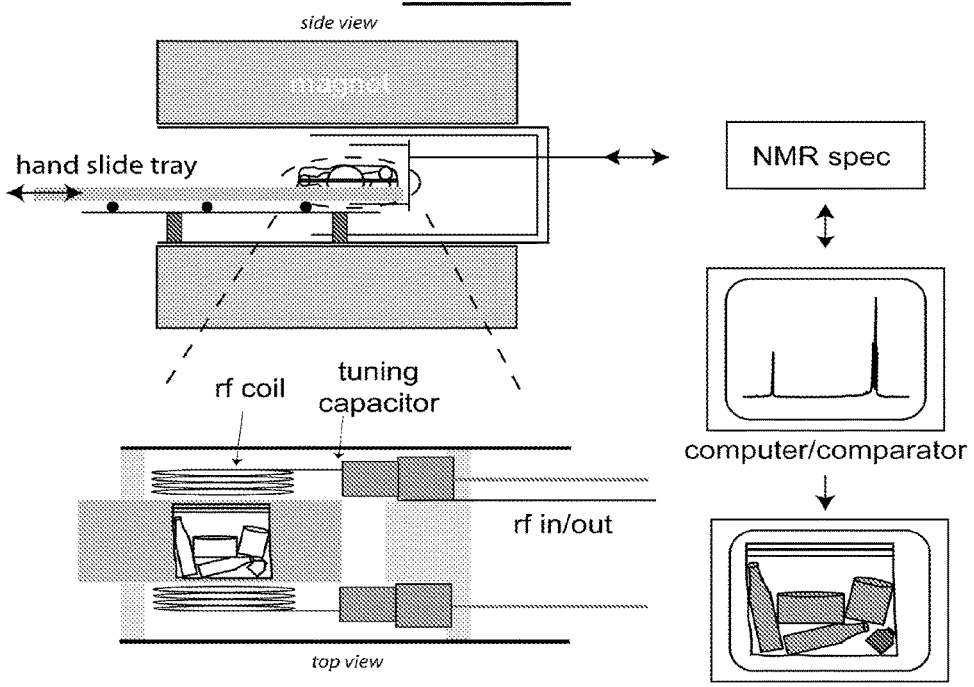
FIG. 13 depicts a security conveyor device with a hand slide tray for a bag and including an exemplary probe according to specific embodiments and configured for scanning a bag containing liquids in metallic and/or non metallic containers.
Figure 14:
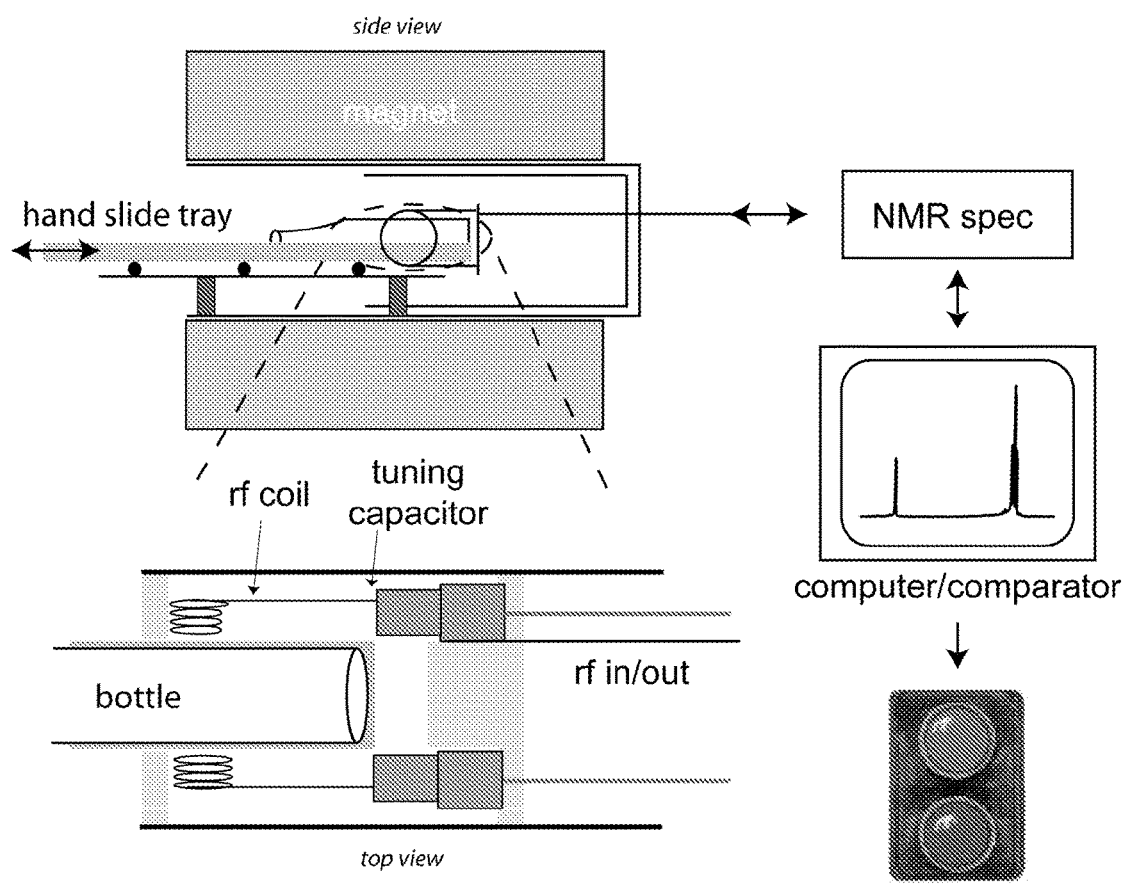
FIG. 14 depicts a security conveyor device with a hand slide tray for a bottle and including an exemplary probe according to specific embodiments and configured for scanning a metallic and/or non metallic container.

According to specific embodiments one or more probes as described herein can be configured to be installed in a security scanner, e.g., at a building or airport, for routing scanning of containers for the presence of contraband materials. FIG. 11 depicts a security conveyor device including an exemplary probe according to specific embodiments and configured for scanning a bag containing liquids in metallic and/or non metallic containers. FIG. 12 depicts a security conveyor device with a hand slide tray for a baggy and including an exemplary probe according to specific embodiments and configured for scanning a bag containing liquids in metallic and/or non metallic containers. FIG. 13 depicts a security conveyor device with a hand slide tray for a bottles and including an exemplary probe according to specific embodiments and configured for scanning a metallic and/or non metallic container. According to specific embodiments, the invention provides an improved scanning device for airport security.

Conclusion

The discussion above is generally applicable to the aspects and embodiments of the present invention. Moreover, modifications can be made to the methods, apparatus, and systems described herein without departing from the spirit and scope of the invention as claimed, and the invention can be put to a number of different uses including the following:

The use of an NMR probe configured to accept a sealed container or an NMR system as set for the herein, for performing any of the methods and assays set forth herein.

The use of an NMR probe or system as described herein for performing noninvasive analysis of a sealed container, e.g., for analysis of one or more contaminants, as set forth herein.

A kit comprising one or more standard solutions of contaminant (e.g., acetic acid titration samples) in a sealed container, for use in the methods, devices or systems of the present invention. Optionally, the kit further comprises an instruction manual for performing the methods of the present invention.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of analyzing one or more contents of one or more sealed radio shielding containers, the method comprising:
   providing a nuclear magnetic resonance (NMR) spectrometer and an NMR probe configured to accept a portion of a sealed radio shielding container, all of the sealed radio shielding container, or a portion or all of a plurality of sealed radio shielding containers;
   positioning said portion of the sealed radio shielding container, all of the sealed radio shielding container, or a portion or all of the plurality of sealed radio shielding containers within a data collection region of the NMR probe;
   establishing a homogeneous static magnetic field across the data collection region;
   applying an amplitude and frequency swept shaped radio frequency (RF) pulse, wherein the applied RF pulse has a frequency between about 3 to about 10 MHz, and wherein the RF pulse is a high powered pulse of at least 0.5 kW;
   collecting an NMR spectrum;
   applying a reference RF pulse to stimulate precession of a heteronuclear frequency reference sample in the probe, wherein at least a portion of the heteronuclear frequency reference sample is mounted inside the data collection region of the NMR spectrometer and wherein the heteronuclear frequency reference sample is external to the sealed radio shielding container;
   collecting a reference NMR spectrum; and
   analyzing one or more peaks in the NMR spectrum using the reference NMR spectrum, thereby analyzing one or more contents of the one or more sealed radio shielding containers.

2. The method of claim 1, further wherein the power of the RF pulse ranges from 0.5 kW to 10 kW.

3. The method of claim 1, further wherein the shaped RF pulse is one or more of:
   a frequency and amplitude modulated adiabatic half soliton pulse;
   one or more adiabatic RF pulses;
   one or more adiabatic RF pulses in a mixture of pulses;
   a half soliton hyperbolic pulse;
   one or more linear and non-linear frequency and amplitude sweeps; and
   one or more mixtures of constant and variable amplitude and frequency changes.

4. The method of claim 1, further comprising:
   applying a near field mid-range high powered shaped frequency RF signal selected to provide a detectable NMR precession signal from substances in conducting radio shielding containers to perform NMR.

5. The method of claim 1, further comprising:
   applying high power shaped RF pulses to the outside of a metal or RF shielding container such that the attenuation of the RF amplitude by the metal container presents a low power broadband excitation pulse to the container contents; and
   wherein the low power broadband excitation pulse causes large free precession signals from the contents which are then detected outside the container.

6. The method of claim 1, further comprising:
   broadcasting shaped adiabatic high power micro-second (µS) time scale RF pulses; and
   receiving and analyzing longer time scale low power RF free precession signals.

7. The method of claim 1, wherein the heteronuclear frequency reference sample comprises perfluorocyclohexane used to reference the field and frequency via $^{19}F$ NMR spectroscopy.

8. The method of claim 1, wherein the radio shielding container comprises a metallic or conducting container.

9. The method of claim 1, wherein the NMR spectrometer further comprises one or more shim coils, and wherein establishing the homogeneous static magnetic field across the data collection region comprises adjusting the one or more shim coils.

10. A nuclear magnetic resonance (NMR) probe configured to position all or portions of one or more sealed radio shielding containers within an NMR spectrometer, the probe comprising:
    a body structure having a cavity disposed at a first end of the body structure, said cavity being adapted for receiving said sealed radio shielding containers;
    a first radio frequency (RF) coil positioned proximal to the cavity and the sealed radio shielding containers;
    an external heteronuclear frequency reference sample in a separate container positioned at least partially within the first RF coil;
    an RF field generator able to generate a shaped frequency swept and amplitude variable RF signal, and
    a tuning capacitor coupled at a first position to the RF coil and coupled at a second position to a length of coaxial cable configured for connection to the NMR spectrometer.

11. The NMR probe of claim 10, wherein the first RF coil comprises 12 gauge copper wire wound as an eight turn 1 cm diameter split solenoid coil.

12. The NMR probe of claim 10, wherein the first RF coil comprises a coil used for both transmitting and receiving RF pulses at both the reference and the detection frequencies.

13. The NMR probe of claim 10, further comprising a second RF coil positioned distal to the first RF coil.

14. The NMR probe of claim 10, further comprising components for generating one or more magnetic field gradients, wherein the components are coupled to the body structure.

15. The NMR probe of claim 10, further comprising a tuning capacitor coupled to the first RF coil, wherein the tuning capacitor comprises one or more non-magnetic 0-10 picofarad high power RF capacitors.

16. A system for analyzing contents of one or more sealed radio shielding containers, comprising:
    the NMR probe of claim 10;
    an NMR spectrometer comprising a body structure, a magnet housed within the body structure, a bore proximal to the magnet and configured to receive the NMR probe, thereby positioning a portion of the sealed radio shielding container within a magnetic field generated by the magnet, and an amplifier configured for coupling to a first position on the NMR probe; and
    a receiver system configured for electronic communication with the NMR probe, the receiver system comprising a preamplifier configured for coupling to a second position on the NMR probe and a detector in communication with the preamplifier.

17. A security scanner system for screening items for contraband comprising:
    the NMR probe of claim 10;
    a scanner housing having a cavity capable of holding said items;
    a receiving opening for receiving said items into said cavity;

said NMR probe configured within said housing to position items placed within said cavity within an NMR spectrometer.

* * * * *